(12) United States Patent
Seitzinger

(10) Patent No.: US 6,213,777 B1
(45) Date of Patent: Apr. 10, 2001

(54) APPARATUS FOR CLEANING AND STORING DENTAL APPLIANCES

(75) Inventor: Jeana L. Seitzinger, Onawa, IA (US)

(73) Assignee: Board of Regents of the University of Nebraska, Lincoln, NE (US)

(*) Notice: Subject to any disclaimer, the term of this patent is extended or adjusted under 35 U.S.C. 154(b) by 0 days.

(21) Appl. No.: 09/305,645

(22) Filed: May 5, 1999

(51) Int. Cl.[7] .................................................. A61C 17/00
(52) U.S. Cl. .......................................... 433/229; 206/63.5
(58) Field of Search ................... 433/77, 229; 206/63.5, 206/83, 361, 362; 132/308, 309, 310; 134/135, 137; 220/735, 736

(56) References Cited

U.S. PATENT DOCUMENTS

| | | | |
|---|---|---|---|
| 1,584,261 | * | 5/1926 | Vuolo ................................. 206/362.1 |
| 2,627,276 | * | 2/1953 | Eggleton ............................... 134/143 |
| 4,179,040 | | 12/1979 | Bateman et al. ....................... 220/410 |
| 5,201,411 | * | 4/1993 | Elkins et al. ............................ 206/83 |
| 5,298,077 | | 3/1994 | Saarela et al. ........................... 134/6 |
| 5,314,543 | | 5/1994 | Elkins et al. ............................. 134/1 |
| 5,402,810 | * | 4/1995 | Donley ................................. 134/135 |
| 5,566,823 | * | 10/1996 | Summers ........................... 206/209.1 |

* cited by examiner

Primary Examiner—John J. Wilson
Assistant Examiner—Melba Bumgarner
(74) Attorney, Agent, or Firm—Turan P. Odabasi

(57) ABSTRACT

A new and useful apparatus for cleaning and storing dental appliances and similar articles. This apparatus incorporates a container filled with a liquid dentifrice together with an elongated structure to suspend a dental appliance in the dentifrice. The dental appliance can easily be stored in and removed from the apparatus without undue mess or inconvenience to the user.

16 Claims, 2 Drawing Sheets

APPARATUS FOR CLEANING AND STORING DENTAL APPLIANCES

TECHNICAL FIELD

The present invention relates to the fields of dentistry and orthodontics, specifically to a novel apparatus used to store and clean dental appliances.

BACKGROUND OF THE INVENTION

Dental appliances such as dentures, retainers and mouth guards are a necessity for many people. Normal use of such appliances often requires the user to wear the appliance for several hours or more each day. During such normal use, bacteria from the common flora of the human mouth collect on the appliance by adhering to its irregular surface. Proper care and maintenance of the appliance will remove this bacteria and keep the appliance fresh and in good condition. However, proper care and maintenance of such appliances can be a nuisance for their users. A lack of such care can lead to, among other things, an unpleasant odor and taste due to a build up of bacteria on the appliance and neglect of the appliance itself. Neglect of the appliance can cause problems with the proper mechanical operation of the appliance, and thus, the appliance will not function as intended and the user ultimately loses the benefit of the appliance.

Methods for cleaning dental appliances commonly involve the user brushing the appliance with a toothbrush and toothpaste or other dentifrice. Other methods involve soaking the appliance in a specially formulated dentifrice. The dentifrice is usually contained in an ordinary drinking glass, and the appliance is placed in the glass to soak for a given period of time in the dentifrice. These methods, however, require the user to retrieve the appliance from the glass with his or her bare hands or to "fish" the appliance out of the glass using some form of an elongated object. Either method can be time consuming, inconvenient and somewhat messy. Alternative methods of and apparatus for cleaning dental appliances are therefore a useful improvement to the fields of dentistry and orthodontics.

SUMMARY OF THE INVENTION

It is an object of the present invention to disclose an apparatus used to clean and store dental appliances such as dentures, retainers and mouth guards.

Accordingly, the present invention provides for an apparatus comprising a container, an amount of liquid dentifrice contained therein, a lid securable atop said container and removable therefrom, an elongated member attached to the inner surface of said lid so as to extend into said container and said liquid dentifrice when said lid is secured atop said container, a brush and means for securing said brush attached to said elongated member, and means for securing a dental appliance attached to said elongated member.

It is another object of the present invention to disclose an apparatus comprising a container, an amount of liquid dentifrice contained therein, a lid securable atop said container and removable therefrom, an elongated member extending into said container and said liquid dentifrice, a grasping tab extending from the upper end of said elongated member, a brush and means for securing said brush attached to said elongated member, and means for securing a dental appliance attached to said elongated member.

Additional objects, advantages and novel features of the present invention will be set forth in part in the description which follows, and in part will become apparent to those skilled in the art upon examination of the following, or may be learned from practice of the invention.

DESCRIPTION OF THE DRAWINGS

In the accompanying drawings which form a part of this specification and are to be read in conjunction therewith and in which like reference numerals are used to indicate like parts in the various views.

DESCRIPTION OF THE INVENTION

The present invention discloses a new and useful apparatus to be used to clean and store dental appliances such as, but not limited to, dentures, retainers and mouth guards. This apparatus allows the user to easily clean and store his or her appliance in a liquid dentifrice or other cleaning/storage solution and effortlessly retrieve the appliance from the liquid dentifrice without mess or inconvenience.

Figure 1:
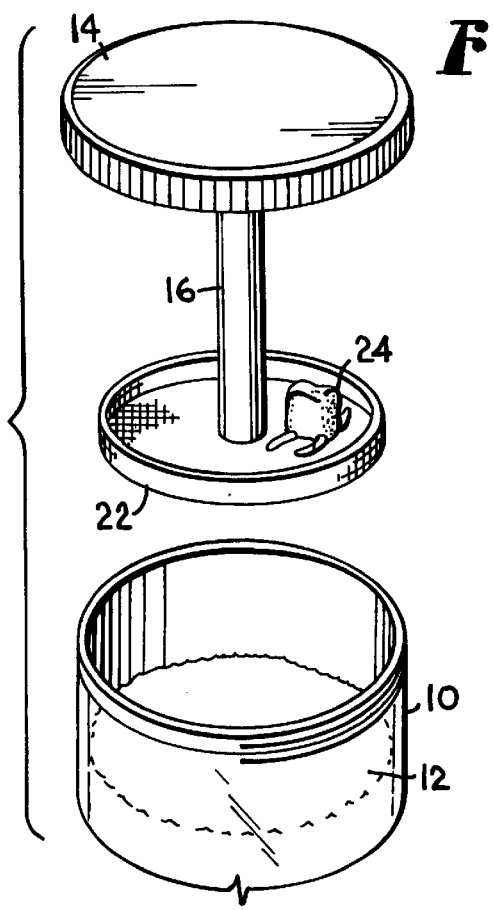
FIG. 1 is an exploded perspective view of a dental appliance cleaning and storage apparatus according to the present invention.
Figure 2:
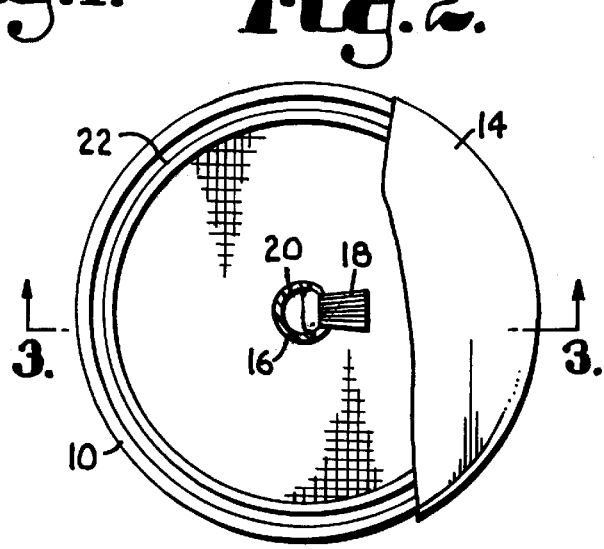
FIG. 2 is an upper plan view of the storage apparatus shown in FIG. 1, parts broken away and shown in cross section to reveal details of construction.
Figure 3:
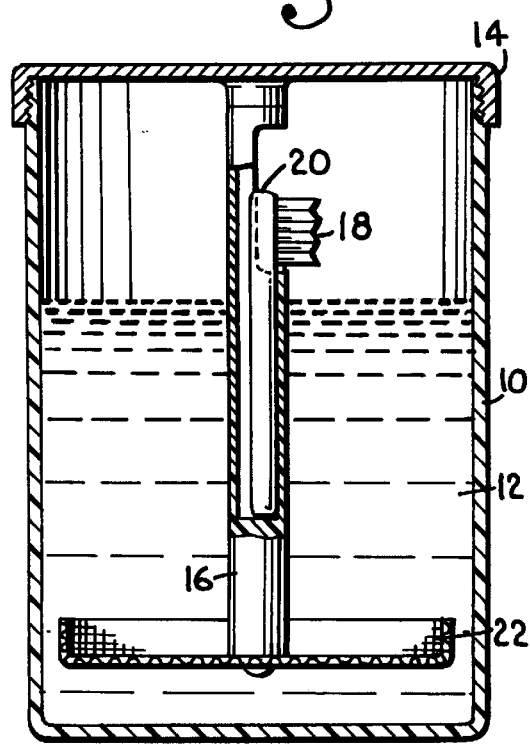
FIG. 3 is a cross sectional view taken generally along line 3—3 of FIG. 2.

As depicted in FIG. 1 and FIG. 3, a first embodiment of the apparatus consists of a container 10 containing an amount of liquid dentifrice 12, a lid 14 securable atop said container 10 and removable therefrom, an elongated member 16 attached to the inner surface of said lid 14 so as to extend into said container 10 and said liquid dentifrice 12 contained therein, a brush 18 and a hollow 20 formed in said elongated member 16 which functions to secure said brush 18 to said elongated member 16, and a basket 22 attached to said elongated member 16 which acts to secure a dental appliance 24 to said elongated member 16. Other suitable structures, as described later, may also be used to secure said brush 18 and said dental appliance 24 to said elongated member 16.

Use of the present invention is quite uncomplicated. The user must first pour an amount of liquid dentifrice 12 such as, but not limited to, mouthwash and/or other specially formulated dental cleaners such as Efferdent™ into the container 10. For proper operation, this amount must at least be enough to cover the basket 22 and the dental appliance 24 secured therein, although the user can employ more than this amount to also cover the brush 18. The user then removes his or her dental appliance 24 and places it in the basket 22. Next, the user inserts the lid 14, to which are attached the elongated member 16, the brush 18, the basket 22 and the dental appliance 24 secured therein into the container 10 and the liquid dentifrice 12 contained therein and secures the lid 14 to the top ofthe container 10.

To remove the appliance, the user simply removes the lid 14 from the container 10, simultaneously withdrawing the attached elongated member 16, the basket 22 and the dental appliance 24 secured thereto from the liquid dentifrice 12 and the container 10. All but a slight residue of liquid dentifrice 12 will drain from the dental appliance 24 as it is removed from the container 10 and will remain therein. The user can then either withdraw the dental appliance 24 from the basket 22 and begin use of the appliance, or he or she may use the brush 18 to additionally clean the dental appliance 24 before use.

Figure 4:
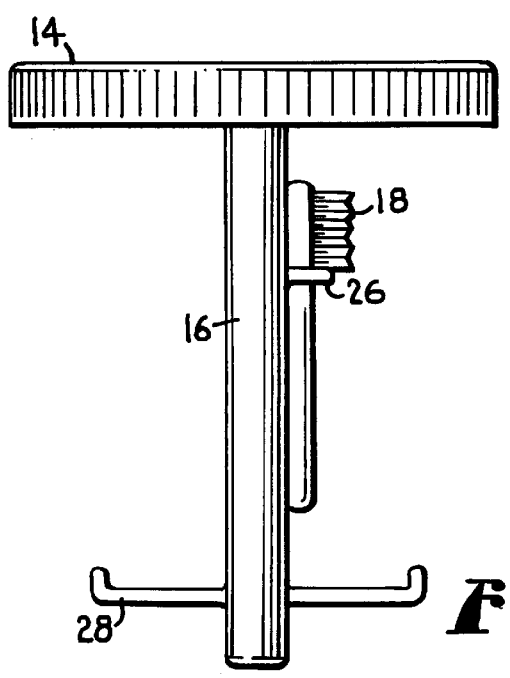
FIG. 4 is a side elevational view of a lid and an elongated member according to a second embodiment of the present invention, the lid and the elongated member shown removed from the container.

A second embodiment of the apparatus is depicted in FIG. 4. This embodiment consists of a lid 14, an elongated member 16 attached to the inner surface of said lid 14, a brush 18 and a hook extending from said elongated member 26 which functions to secure said brush 18 to said elongated member 16, and a hook or set of hooks 28 attached to said elongated member 16 which acts to secure a dental appliance to said elongated member 16. Although not depicted in FIG. 4, this apparatus is clearly meant to be inserted into a container filled with an amount of liquid dentifrice. The lid 14 is meant to be secured atop said container, similar to the apparatus depicted in FIG. 3, and is meant to be removable therefrom, as depicted in FIG. 1.

Figure 5:
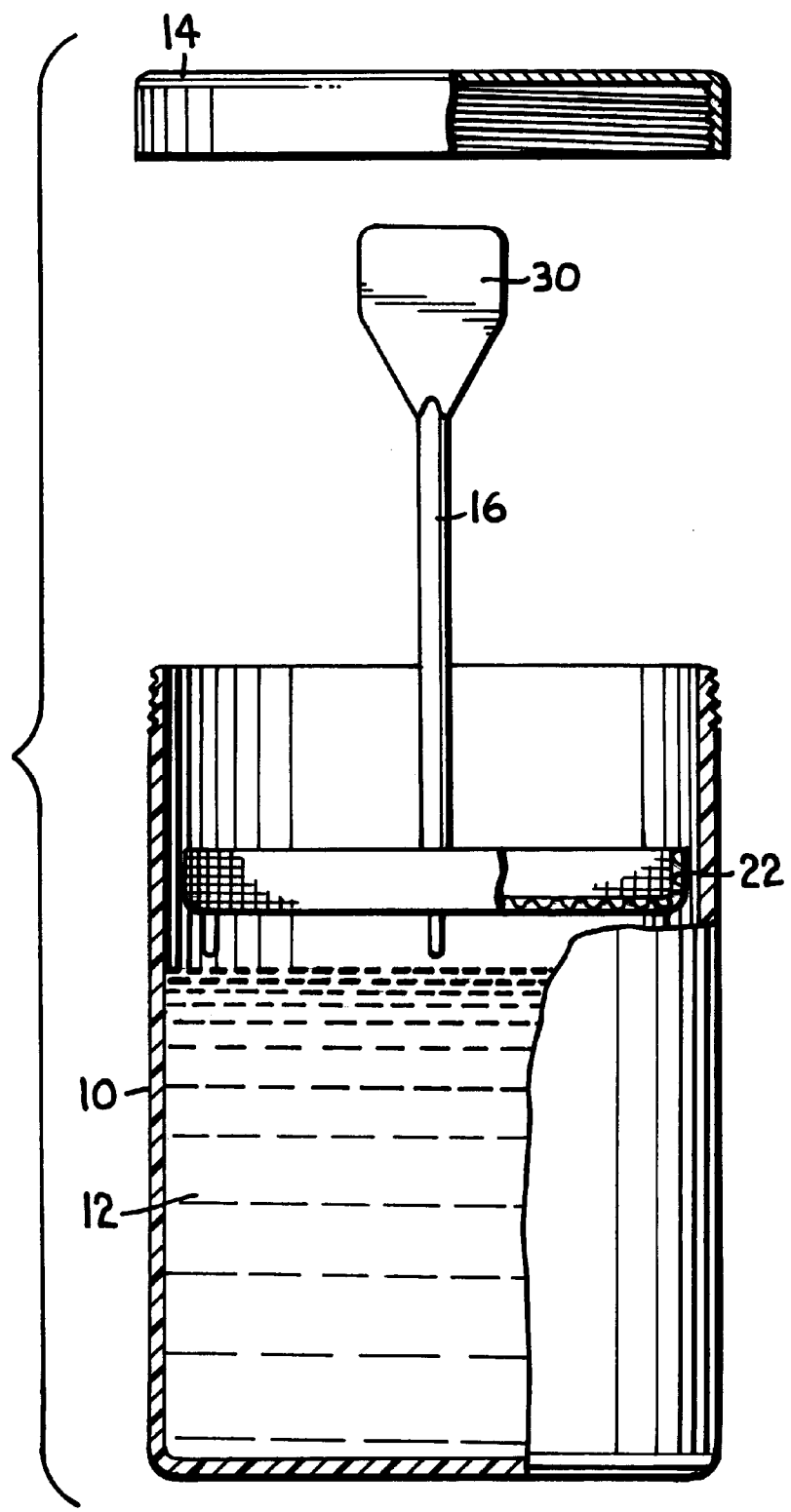
FIG. 5 is an exploded side elevational view of a third embodiment of the present invention, parts broken away and shown in cross section to reveal details of construction.

A third embodiment of the apparatus is depicted in FIG. 5. This embodiment consists of a container 10 containing an amount of liquid dentifrice 12, a lid 14 securable atop said container 10 and removable therefrom, an elongated member 16 that extends into said container 10 and said liquid dentifrice 12 contained therein, a grasping member 30 extending from the upper end of the elongated member 16, a basket 22 attached to the lower end of said elongated member 16 which acts to secure a dental appliance to said elongated member 16. Although not shown in FIG. 5, this apparatus is also meant to include a brush and means to attach said brush to said elongated member 16 as in the first and second embodiments of the apparatus and as depicted in FIG. 3 and FIG. 4.

In this third embodiment, the lid 14 is not attached to the elongated member 16 or the basket 22 securing the dental appliance. This allows the user to remove the lid 14 from the container 10 while leaving the elongated member 16 and the basket 22 securing the dental appliance in the container 10 and the liquid dentifrice 12. The grasping member 30 allows the user to grasp and remove the elongated member 16 and the basket 22 securing the dental appliance from the container 10 and the liquid dentifrice 12 without undue mess. The grasping member 30 also allows the user to re-insert the elongated member 16 and the basket 22 securing the dental appliance into the container 10. Again, the lid 14 is meant to be securable to the top of the container and removable therefrom, as in the first and second embodiments of the apparatus, and as depicted in FIG. 1.

In addition to the forgoing, the means for securing the brush and the dental appliance to the elongated member may include, but are not limited to a strap or series of straps and rings or formations capable of having objects inserted into them or secured to them. In relation to dental appliances, said means may also consist of implements specially designed or tailored to hold a specific individual's dental appliance. Also, said means may include a plurality of baskets, hooks or other means for securing dental appliances to the elongated member, provided the elongated member is of sufficient length to adequately support such additional means.

Ideally, all of the members of the present invention are formed from high quality plastic, polystyrene and/or nylon. However, glass and/or any non-corrosive metal (such as, but not limited to, stainless steel or aluminum) will also perform adequately.

What is claimed is:

1. An apparatus for cleaning and storing dental appliances comprising:

(a) a container holding a liquid dentifrice, (b) a lid securable atop said container and removable therefrom, (c) an elongated member attached to the inner surface of said lid so as to extend into said container and the liquid dentifrice when said lid is secured atop said container, (d) means for securing the dental appliances to said elongated member, (e) a brush, and (f) means for securing said brush to said elongated member.

2. An apparatus as specified in claim 1 wherein said means for securing the dental appliances to said elongated member consists of a basket or other perforated curved structure.

3. An apparatus as specified in claim 1 wherein said means for securing the dental appliances to said elongated member consists of a hook or series of hooks.

4. An apparatus as specified in claim 1 wherein said means for securing said brush to said elongated member consists of a hollow formed in said elongated member and means for entry and egress of said brush from said hollow.

5. An apparatus as specified in claim 1 wherein said means for securing said brush to said elongated member consists of a hook or series of hooks.

6. An apparatus for cleaning and storing dental appliances comprising:

(a) a container holding a liquid dentifrice, (b) a lid securable atop said container and removable therefrom, (c) an elongated member attached to the inner surface of said lid so as to extend into said container and the liquid dentifrice when said lid is secured atop said container, (d) a first securing structure attaching the dental appliances to said elongated member, (e) a brush, and (f) a second securing structure attaching said brush to said elongated member.

7. An apparatus as specified in claim 6 wherein said first securing structure is a basket.

8. An apparatus as specified in claim 6 wherein said first securing structure is a hook.

9. An apparatus as specified in claim 6 wherein said second securing structure is a hook.

10. An apparatus as specified in claim 6 wherein said second securing structure consists of a hollow formed in said elongated member securing said brush to said elongated member.

11. An apparatus for cleaning and storing dental appliances comprising:
   (a) a container holding a liquid dentifrice,
   (b) a lid securable atop said container and removable therefrom,
   (c) an elongated member extending into said container and the liquid dentifrice,
   (d) a first securing structure attaching the dental appliances to said elongated member,
   (e) a brush, and
   (f) a second securing structure attaching said brush to said elongated member.

12. An apparatus as specified in claim 11 wherein said first securing structure is a basket.

13. An apparatus as specified in claim 11 wherein said first securing structure is a hook.

14. An apparatus as specified in claim 11 wherein said second securing structure is a hook.

15. An apparatus as specified in claim 11 wherein said second securing structure consists of a hollow formed in said elongated member securing said brush to said elongated member.

16. An apparatus as specified in claim 11 whereas said elongated member has a grasping member for removing said elongated member from the container.

* * * * *